United States Patent [19]

Karwoski et al.

[11] Patent Number: 4,632,842
[45] Date of Patent: Dec. 30, 1986

[54] GLOW DISCHARGE PROCESS FOR PRODUCING IMPLANTABLE DEVICES

[75] Inventors: Theodore Karwoski; Yasuo Matsuzawa, both of Nashua, N.H.

[73] Assignee: Atrium Medical Corporation, Hollis, N.H.

[21] Appl. No.: 747,011

[22] Filed: Jun. 20, 1985

[51] Int. Cl.$^4$ .............................................. B05D 3/06
[52] U.S. Cl. ......................................... 427/2; 427/41
[58] Field of Search ................ 427/2, 41; 128/334 R; 604/266; 623/1, 12

[56] References Cited

U.S. PATENT DOCUMENTS

| | | | |
|---|---|---|---|
| 3,068,510 | 12/1962 | Coleman | 18/2 |
| 3,663,265 | 5/1972 | Lee et al. | 117/93.1 |
| 3,839,743 | 10/1974 | Schwarcz | 3/1 |
| 4,076,916 | 2/1978 | Lagow | 526/43 |
| 4,188,426 | 2/1980 | Auerbach | 427/40 |
| 4,193,138 | 3/1980 | Okita | 427/2 |
| 4,229,838 | 10/1980 | Mano | 427/2 |
| 4,252,848 | 2/1981 | Datta et al. | 428/64 |
| 4,264,750 | 4/1981 | Anand et al. | 525/356 |
| 4,286,341 | 9/1981 | Greer et al. | 3/1.4 |
| 4,349,582 | 9/1982 | Beerwald et al. | 427/38 |
| 4,404,256 | 9/1983 | Anand et al. | 428/409 |
| 4,488,954 | 12/1984 | Hatada et al. | 204/169 |

FOREIGN PATENT DOCUMENTS 54-56672  7/1979  Japan .

OTHER PUBLICATIONS

"Improving the Inner Surface of Polymer Tubes by Subjecting to Glow Discharge", 1977, abstract, Toray Industries.
Garfinkle, Hoffman, Ratner, Reynolds, & Hanson—'-'Effects of a Tetrafluoroethylene Glow Discharge on Patency of Small Diameter Dacron Vascular Grafts", vol. XXX, Trans Am. Soc. Artif. Intern. Organs, 1984—pp. 432-440.
Yasuda, H.—"Glow Discharge Polymerization", vol. 16, Journal of Polymer Science: Macromolecular Reviews, pp. 199-293, 1981.
Yasuda & Hirotsu—"Critical Evaluation of Conditions of Plasma Polymerization", Materials Research Center, University of Missouri—Rolla, Rolla, Missouri, 1977.
Yasuda & Hsu, "Some Aspects of Plasma Polymerization of Fluorine-Containing Organic Compounds. II. Comparison of Ethylene and Tetrafluoroethylene", vol. 16, Journal of Polymer Sci., 415-425 (1978).
Soong & Bell—"The Effects of Hydrogen on the Plasma Polymerization of Tetrafluoroethylene", vol. 21, Polymer Engineering & Science, Aug., No. 11 (1981).
Morosoff & Yasuda—"Plasma Polymerization of Tetrafluoroethylene II. Capacitive Radio Frequency Discharge", vol. 23, Journal of Applied Polymer Science pp. 3449-3470, (1979).

(List continued on next page.)

Primary Examiner—John H. Newsome
Attorney, Agent, or Firm—Lahive & Cockfield

[57] ABSTRACT

Disclosed is a method of producing implantable prosthetic devices, e.g., tubular vascular prostheses having a substantially non-thrombogenic inside surface and a biocompatible outside surface. The method involves deposition onto an elongate substrate, e.g., a porous tubular substrate, of a fluorine-containing coating by inducing glow discharge progressively along the length of a tubular reaction vessel. A polymerizable fluorine-containing gas is flowed through the tubular substrate and a portion of the gas migrates radially to traverse the pores of the substrate. An RF field is applied to successive volumes of the gas within the vessel and tube. A substantially non-thrombogenic fluorinated coating with a first fluorine to carbon ratio deposits and bonds to the inside surface of the substrate, and a fluorinated biocompatible cross-linked coating with a lower F/C atomic ratio than the inside coating deposits and bonds to the outside surface of the substrate. The method of the invention can produce uniform coatings containing fluorine over the surface of elongated substrates. The coatings can be engineered to have a very low surface energy and to be essentially non-thrombogenic.

25 Claims, 6 Drawing Figures

OTHER PUBLICATIONS

Masuoka & Yasuda—"Plasma Polymerization of Tetrafluoroethylene III. Reproducibility and Effects of Substrate and Reactor Materials", vol. 19, Journal of Polymer Sci., pp. 2937-2946 (1981).

Morosoff & Yasuda—"Plasma Polymerization of Tetrafluoroethylene. III. Capacitive Audio Frequency (10 kHz) & AC Discharge", vol. 23, Journal of Applied Polymer Sci., pp. 3471-3488, (1979).

Yanagihara & Yasuda, "Plasma Polymerization of Tetrafluoroethylene IV. Comparison of Ethylene & Tetrafluoroethylene by Measurement of Electron Temperature & Density of Positive Ions", vol. 20, Journ. of Polymer Sci., pp. 1833-1846 (1982).

Yasuda & Gazicki, "Biomedical Applications of Plasma Polymerization & Plasma Treatment of Polymer Surfaces", vol. 3, Biomaterials—pp. 68-77, Apr. (1982).

Cohen & Baddour—"Surface Modification of Low Density Polyethylene in a Fluorine Gas Plasma", vol. 22, Polymer, pp. 361-371, Mar. (1981).

Corbin, Cohen & Baddour—"Kinetics of Polymer Surface Fluorination: Elemental and Plasma-Enhanced Reactions", vol. 23, Polymer, pp. 1546-1548, Sep. (1982).

Yasuda & Hirotsu—"Distribution of Polymer Deposition in Plasma Polymerization. II. Effect of Reactor Design", vol. 16, Journal of Polymer Science: Polymer Chemistry Edition, pp. 313-326 (1978).

Yasuda—"Glow Discharge Polymerization", vol. 3, pp. 102-122, Contemporary Topics in Polymer Science, (1979).

Yasuda et al, "Glow Discharge Polymers as Coatings for Implanted Devices", pp. 109-113, ISA (1981).

Matsuzawa & Yasuda, "Semi-Continuous Plasma Polymerization Coating Onto the Inside Surface of Plastic Tubing", pp. 2-21, Dept. of Chemical Engineering & Graduate Center for Materials Research University of Missouri-Rolla, Rolla, MO 65401.

Garfinkle et al, "Improved Patency in Small Diameter Dacron Vascular Grafts After a Tetrafluoroethylene Glow Discharge Treatment", p. 337, Second World Congress on Biomaterials, 10th Ann. Mtg., Apr. 27-May 1 (1984).

Ratner et al, "RF Plasma-Deposited Films as Model Substrates for Studying Biointeractions", p. 189, Second World Congress on Biomaterials, 10th Ann. Mtg. Apr. 27-May 1, 1984.

Yasuda et al, "Blood Surface Interaction Investigated with Ultrathin Coatings of Glow Discharge Polymers Applied Onto the Inner Surface of Small Diameter Silastic Tubing"—Second World Congress on Biomaterials, 10th Ann. Mtg., Apr. 27-May 1, 1984.

Hoffman, Garfinkle, Ratner, "Surface Modification of Small Diameter Dacron Vascular Grafts After a Tetrafluoroethylene Glow Discharge Treatment"—Second World Congress on Biomaterials—10th Annual Mtg., Apr. 27-May 1, 1984.

Dr. Hirotsugu K. Yasuda Abstract, "Method and Design of Equipment to Coat Inside Surface of Long Plastic Tubing", Univ. of Missouri.

GLOW DISCHARGE PROCESS FOR PRODUCING IMPLANTABLE DEVICES

BACKGROUND OF THE INVENTION

This invention relates to methods of coating materials intended for implantation and to the coated materials. More particularly, it relates to the deposition of fluoropolymer coatings on the surfaces of tubular and other substrates to improve the substrate's biocompatibility properties.

Devices intended for use within the body such as vascular prostheses often comprise materials which have limited biocompatibility and non-thrombogenic properties. The surfaces of such devices may be coated to improve biocompatibility without compromising other properties such as durability and flexibility. One technique for coating such materials is plasma polymerization. The surfaces of tubes comprising polymeric materials can be modified by deposition of a thin layer of a fluorine-containing polymer using plasma polymerization techniques, also known as glow discharge. The technique involves introducing a polymerizable organic monomer in the gaseous state into a vacuum containing the substrate material to be coated. The gas is then subjected to an electric discharge to initiate polymerization reactions, generating ions or free radicals which react with and deposit on the substrate. The polymer formed is normally deposited as a thin layer over the substrate material present in the reaction vessel. The bulk substrate characteristics are preserved, but the surface properties, which are major determinants of biocompatibility and non-thrombogenicity, can be modified or improved by plasma polymerization.

Plasma polymerization was used to prepare biomaterials as early as 1969 (J. R. Hollahan, et al., *J. Appl. Polymer Science* 13, 807, 1969). A leader in the area, Dr. H. Yasuda, conducted blood coagulation studies on glow discharge (plasma) polymer surfaces in 1976. A. W. Haln investigated biomedical applications as reported in an *NBS Spec. Publ.* 415 (May 1975). More recently, other investigators have also reported the results of experiments on plasma polymerization treatments of substrates intended for use within the body.

There has been a general lack of success and relatively few publications in the plasma polymerization biomaterials area (Yasuda, H. and Gazicki, M., Biomedical Applications of Plasma Polymerization in Plasma Treatment of Polymer Surfaces, *Biomaterials* vol. 3: 68, April 1982). It is believed that no glow discharge-coated implantable devices are available commercially, because the problems with the prior art are several. The difficulties with plasma polymerization techniques include variable plasma monomer forms in the gas, variable energies introduced to initiate polymerization, infinitely adjustable gas pressures and concentrations, and poor reactor designs. The prior art techniques generally produce non-uniform coatings or non-continuous coatings, especially on larger substrates. For example, some methods of coating tubes result in a heavy coating accumulation near the end of the tubing where the flow of gas is initiated. In treating the surfaces of elongate substrates there are typically regions along the length of the surface which are uncoated or which have a coating composition different from that intended.

Much of the prior art discloses substrate "treatment" as opposed to substrate "coating". "Treatment" involves extracting atoms and substituting others within the surface of the substrate, for example, a hydrogen atom in a polymer substrate is extracted and replaced with a fluorine atom. For example, U.S. Pat. No. 4,264,750 discloses a process whereby the surface of a hydrocarbon polymer may be fluorinated by replacing hydrogen atoms with a fluorinated species. "Treatment" techniques are generally limited to gases that will not polymerize, but rather form species which replace atoms in the substrate surface. The coating process, on the other hand, involves the build-up of a covalently bonded coating onto a substrate. This technique results in a three-dimensional cross-linked network upon the existing surface of the substrate.

It is an object of this invention to provide cross-linked polymerized coatings by glow discharge on the surfaces of elongate, e.g., tubular, substrates, and to control the ion density and field strength along the length of the tubes during plasma polymerization to provide a uniform coating. Another object is to coat both the inside and outside of a porous tube, so that the fluorine to carbon (F/C) atomic ratio along the length of the tube is substantially uniform, at least on its inside surface, and the F/C ratio of the coating on the interior surface of the tube is greater than the F/C ratio on the exterior. It is another object of the invention to provide a method for producing an F/C ratio gradient in a fluorine-containing coating through a porous substrate wall. Another object is to provide a coating comprising a substantially uniform three-dimensional, cross-linked fluoropolymer, covalently bonded onto a surface, and to provide prosthetic devices or other devices intended for implantation having a low surface energy. Another object of the invention is to provide a method of uniformly and reproducibly coating materials intended for implantation with a fluorine containing, low-energy surface coating having a F/C ratio greater than 1.5. Another object is to provide a porous, coated elastic prosthetic device having a coating which does not break when the device is stretched. Yet another object is to provide a prosthetic device with a thin film coating to achieve a substantially non-thrombogenic blood contact surface. Another object is to provide a process for uniformly coating implantable devices which does not alter or significantly change any mechanical or physical properties of the substrate, except those related to surface energy and composition.

These and other objects of the invention will be apparent from the description and claims which follow.

SUMMARY OF THE INVENTION

Broadly, it has been discovered that the surfaces of elongate organic substrates may be provided with a substantially uniform, very low surface energy coating by the use of glow discharge conducted in a tubular reaction vessel. To achieve the coating, one establishes a flow of a fluorine-containing gas through the tubular reactor and then applies an RF field within a portion of the reactor vessel, while moving one of the field and the substrate. By controlling the gas pressure at the inlet end and outlet end of the reactor, a substantially constant density of available reactive species can be maintained within the volume of the RF field adjacent the substrate surface. Furthermore, provided the gas in the tube is substantially free or contains only a low concentration of oxidizing agents such as oxygen or oxygen containing compounds, and provided the fluorine-containing gas has an F/C atomic ratio greater than 1.5, e.g., 2, the coating which results can have an F/C ratio greater than 1.5.

Using the process of the invention, coatings having F/C ratios of of 1.7 to 1.8 have routinely been achieved, and ratios approaching 2.0 are possible. Such coatings are characterized by extremely low surface energies. Typically, water contact angles of 140° or higher may be achieved. Such coatings provide the surface with outstanding non-thrombogenic properties. If used within the lumen of hollow devices through which blood flows, such surface coating appear to be essentially free of the tendency to induce formation of thrombi.

Preferably, in the practice of this invention, the substrate is held stationary and the RF field is moved; the gas is tetrafluoroethylene; and the substrate comprises polyethylene terephthalate, e.g., a material such as DuPont's Dacron or Mylar.

The substrate may comprise a fiber, thread, rod, or a porous or non-porous web. In one particularly useful practice of the invention, the substrate is a porous tube, and the process results in a tubular vascular prosthesis having a substantially non-thrombogenic inside surface and a biocompatible outside surface. This embodiment of the method involves placing an organic tubular substrate, defining pores and having a selected outside diameter, within the tubular reaction vessel. A fluorine-containing gas, preferably substantially free of oxygen or oxygen compounds, is flowed through the tubular substrate within the vessel at a sub-atmospheric pressure. During flow through the tubular substrate, a portion of the gas diffuses through pores in the substrate. At the same time, an RF field is applied to a portion of the volume of the gas within the reactor vessel, and one of the RF field and the tubular substrate is moved.

This results in deposit along the length of the substrate of a substantially non-thrombogenic, cross-linked coating bonded to the inside surface of the substrate having a first F/C ratio, and a biocompatible cross-linked coating bonded to the outside surface of the substrate having an F/C ratio lower than the first. A coating also forms within the pores of the substrate and defines an F/C ratio gradient extending from the inside to the outside of the porous tube wall.

In preferred aspects of this embodiment, the mass flow of the fluorine-containing gas is controlled to maintain a substantially stable density of available reactive species at surfaces of the substrate within the RF field during relative motion. This produces a substantially uniform F/C ratio along the length of the inside surface of the substrate. A uniform coating along the length of the outside surface may also be produced. The tubular reaction vessel preferably has an inside diameter slightly greater than the outside diameter of the tubular substrate, e.g., no more than about one mm, and preferably about 0.2 mm. The gas preferably comprises a fluorine-contained gas having an F/C atomic ratio greater than 2 such as tetrafluoroethylene. Hexafluoroethane mixed with hydrogen may also be used. The gas pressure, flow rate, and RF field strength may be controlled as a means of controlling polymerization to produce an interior coating having an F/C ratio of at least 1.5.

The tubular substrate may comprise a thin fabric, e.g., having a wall thickness less than 0.60 mm. The currently preferred substrate comprises a fabric tube composed of polyethylene terephthalate fibers which are less than approximately 15 microns in diameter. The fabric may be knitted, woven or non-woven. One preferred tubular substrate comprises a woven fabric consisting of circumferentially-oriented threads and longitudinally-oriented threads defining loops which extend radially outwardly between the circumferentially-oriented threads. Prior to coating, the loops are set to return to the loop configuration on release of axial stress on the substrate. Such tubes are elastic, macroscopically smooth, form smooth bends, resist radial collapse and kinking, and may be handled and sutured readily by the surgeon.

BRIEF DESCRIPTION OF THE DRAWINGS

Like reference characters in the respective drawn figures indicate corresponding parts. The dimensions of the threads and their spacing in FIGS. 1 and 2 are not to scale but rather have been drawn to promote clarity of description.

DESCRIPTION

Figure 1:
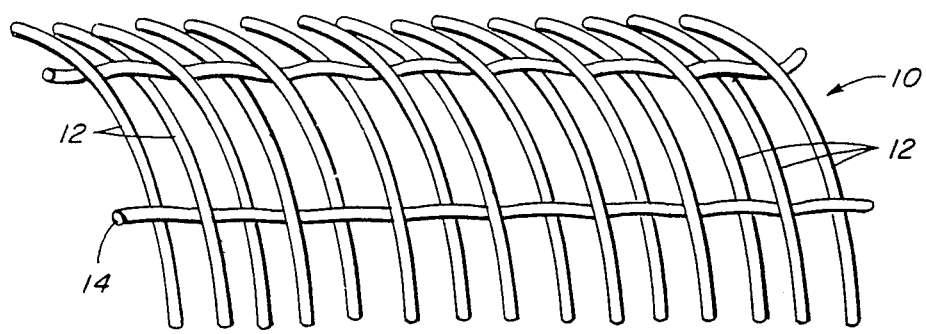
FIG. 1 illustrates schematically a portion of an interwoven fabric tube substrate before compaction.

It has now been discovered that it is possible to deposit a uniform coating of a fluoropolymer having a high fluorine content over the surface of variously shaped organic substrates by exploiting a tubular reactor, controlling gas flow therethrough, and successively exposing relatively small portions of the surface of the substrate to an RF field to induce glow discharge. The coating is characterized by a desireably high fluorine to carbon ratio and by an extremely low surface energy and correspondingly large water contact angle, typically greater than 120° and often exceeding 140°. Such surfaces have been observed to be substanially non-thrombogenic.

Materials coated in accordance with the invention are well suited for fabricating various prosthetic and other devices and objects designed for implantation in the body. By following the teachings disclosed herein, those skilled in the art will be able to produce vascular and other prosthetic devices, sutures, heart valves, shunts, catheters, and other devices. The surfaces of these devices having the polymerized fluorine-containing coating characterized by the properties disclosed herein may be placed in contact with blood with significantly reduced risk of thrombus formation as compared to other materials known to the inventors.

While plasma polymerization techniques are known, including those using fluorine-containing gases such as tetrafluoroethylene, in practice the deposition of such coatings on substrates has been characterized by nonuniformity both from the point of view of the fluorine to carbon ratio and the coating thickness. The unsolved problem has been to control, over the extended surface of a substrate, both the RF field which induces ion generation and the resulting deposition of polymer, and the density of species present in the plasma available for reaction. For example, the present inventors initially experimented with tubular and other elongate substrates disposed between a pair of parallel plate electrodes while maintaining various gas pressures within a large cylindrical reactor. These experiments showed that while the deposition from a plasma of a fluorine-containing polymer could be achieved, its F/C ratio could not be controlled with any precision. Furthermore, the thickness of the coating varied at different regions of the substrate surface, and little or no coating was produced in some regions of the surface. Attempts to coat tubular substrates with such apparatus resulted in uneven fluoropolymer coatings of variable F/C ratio on the exterior of the tube and little or no deposition of polymer on its interior surface. If a gas nozzle is located in the reactor to release gas directly into the interior lumen of a porous tube, a heavy coating deposits adjacent the nozzle whereas along the length of the interior of the tube the coating is again unsatisfactory.

In an attempt to improve upon the process, a method was discovered which can apply a fluorinated polymer coating having a desired F/C ratio substantially uniformly over the entirety of variously shaped elongate surfaces. Furthermore, it was discovered that by suitable control of certain parameters it was possible to deposit novel types of coatings having a very high F/C ratio, i.e., between about 1.5 and 2.0.

Thus, use of the process disclosed herein enables production of fibers, threads, impermeable or permeable webs, tubes, and particularly porous tubes intended for use as vascular prostheses, to be coated with a fluorine-containing polymer substantially uniformly.

The success of the process is believed to be due to the use of a tubular reactor, relative movement of the RF field and the substrate, and the control of polymerization that results from this combination of features. Perhaps the most challenging application of the process is in the area of porous tubes having a length greater than about 15 centimeters which are to be coated on their interior surface. Gas flow characteristics in such tubes are difficult to control because of wall effects and the necessity of having a pressure gradient over the length of the tube to induce gas flow. However, substantially uniform interior coatings having an F/C ratio greater than 1.5 have been deposited using the process described in detail below. Those skilled in the art, without the exercise of invention, will be able readily to coat elongate planar or linear substrates in view of the teaching disclosed herein.

Substrate Selection

Figure 1A:
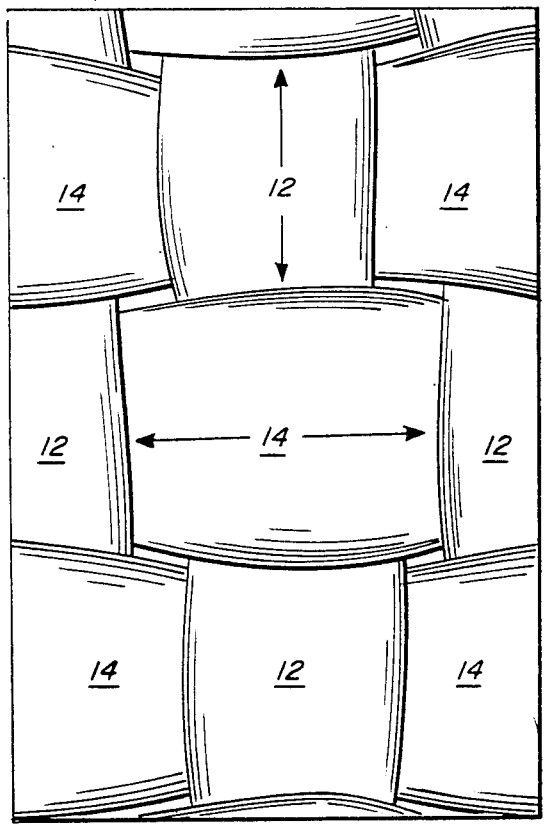
FIG. 1A shows a portion of an interwoven fabric tube before compaction as it appears under the microscope.

Referring to the drawing, FIGS. 1, 1A, 2 and 2A depict (schematically and literally) the currently preferred tubular substrate for manufacturing vascular prostheses in accordance with the method of the invention before and after a compaction treatment. FIGS. 1 and 1A illustrate a section of a fabric tube 10 before it is made elastic by the compaction process. The tube comprises a multiplicity of circumferentially-oriented, fill threads 12 interwoven in a one-over-one relationship with longitudinally oriented non-elastic warp threads 14. The fill threads 12 and warp threads 14 may comprise any synthetic fibrous material, twisted, texturized, or braided yarn, or monofilament. Preferably, however, the threads comprise a material which is relatively non-inflamatory when implanted. Thus, various polyesters, polyamides, polyethylenes, fluorinated polymer fibers and various known polymeric threads may be used. The currently preferred material is polyethylene terephthalate, e.g., material sold by E. I. du Pont de Nemours Co. under the trademark Dacron.

In constructing the fabric tube, it is preferred to employ threads made of one or more yarns, each of which comprise intertwined and/or twisted fine fibers which have a diameter dimension less than about 15 microns, most prefereably less than 7 microns. The small size of the fibers making up the yarns and threads is believed to be responsible in part for the outstanding patency of prosthetic devices made from tubes subsequently coated in accordance with the process disclosed herein.

The woven tube shown in FIG. 1 is illustrative only, and other types of weaves can be treated with success. Thus, the one-over-one weave shown could be replaced with a two-over-one, one-over-two, or two-over-two weave. Other types of weaves may be used provided their threads have a circumferential component which defines the inside diameter of the tube and an axial component which can be formed into microscopic loops as disclosed hereinafter.

The currently preferred tube comprises fibers which are approximately 5-7 microns in cross-section. The warp threads comprise 3 intertwined yarns each of which comprise 75 filaments or fibers to result in a yarn having a denier of 50. The fill threads are 96 filament single yarns having a denier of 100. The use of such materials in fabricating the tube to be treated results in a wall thickness approximately 0.30-0.6 mm as measured from the top of the loops to the inside surface of the tube after treatment.

The length and diameter of the original tube is selected according to biomedical need. Generally, the inside diameter of the tube may range from 3 mm to 2 cm. Smaller tubes are possible.

Figure 2:
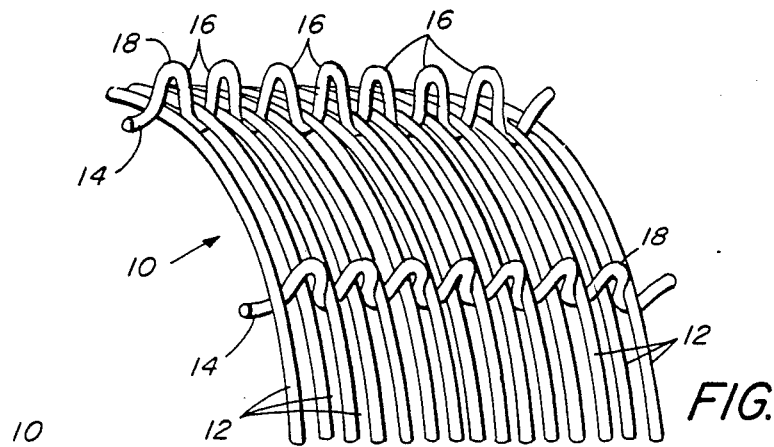
FIG. 2 illustrates schematically the tube portion of FIG. 1 after compaction treatment to produce axially oriented loops formed between the circumferential threads.
Figure 2A:
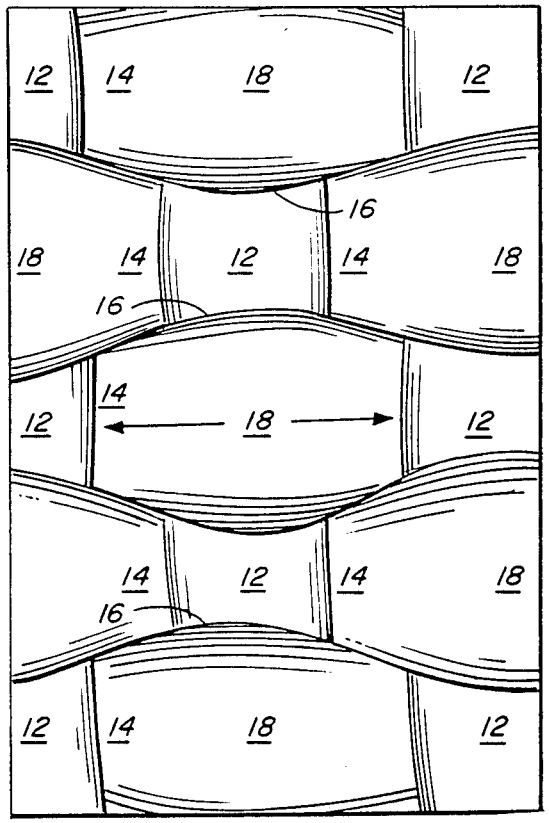
FIG. 2A shows the fabric tube portion of FIG. 1A after compaction treatment as it appears under the microscope.

FIGS. 2 and 2A illustrate the same woven fabric tubular section depicted in FIGS. 1 and 1A after a compaction treatment. Note that the fill threads 12 have been moved closer together and axially compacted and that the warp threads 14 have been formed into loops 16 extending radially upwardly from between the fill threads such that each loop has a single fill thread therebeneath. The top portions 18 of the loops 16 together define a macroscopically smooth surface which visually appears and when touched feels very similar to the non-treated tube. However, the compacted tubes can typically be stretched 20%–70% of their non-stretched, compacted length.

To convert the fabric tube of FIGS. 1 and 1A into that shown in FIGS. 2 and 2A, the tube is moistened and placed on a smooth, cylindrical mandrel having an outside diameter substantially equal to the inside diameter of the tube. The mandrel preferably has a surface of Teflon (du Pont trademark for polytetrafluoroethylene resin), though mandrels composed of other materials may be used. The tube is smoothed out over the mandrel such that the entirety of its inside surface is in contact therewith and then treated, e.g., heated to a temperature of 380° F. for 15 minutes in a convection oven. This heating step is optional but has been found to preset the macroscopically smooth surface. The tube is then allowed to cool back to room temperature. Next, it is compacted on the mandrel by progressively applying axially compression force. This is done manually or mechanically.

In preparing this preferred elastic tube substrate, it is important that the fit between the tube and the mandrel be such that compaction results only in radial extension of the warp fibers upwardly to form the desired loops. A mandrel of insufficient diameter may result in crimping or folding of the fabric, as opposed to the threads of the fabric. The formation of the loops in the threads is responsible for imparting to the tube both a macroscopically smooth exterior surface and the elastic properties characteristic of the prosthetic devices of the invention. Generally, the tube is compressed axially to about 20–70%, preferably about 60%, of its original length, that is, compactly enough to form the loops but not so compact to result in wrinkles or folds in the fabric, as opposed to the threads. The amount of compaction will vary depending on the degree of elasticity desired in the product, on the diameter of the threads, and on the tightness of the weave.

The height and spacing of the loops depends on several factors which include the thickness of the material of the threads, the tightness of the weave, and the length to which the original tube is reduced by compaction.

The fibers are then set in the loop-oriented, compacted form by conventional treatment with a reagent, heat, or some combination thereof while on the mandrel. Using the preferred polyethylene terephthalate threads, excellent results have been achieved by heating the compacted tube to 380° F. for 5–10 minutes. Of course, the temperature to which the tube is heated or whether a reagent treatment is used depends on the particular material from which the threads are made.

The product is a macroscopically smooth, microporous elastic tube section. The loops formed between fill threads return to the loop configuration upon release of tension applied axially to the tube. The loops are smooth and porous because of the fine fibers preferably used, and the compacted fabric has multiple interstices of various dimensions uniformly about its surface which receive connective or other tissue in-growth after implantation. These features facilitate the integration of the tube into surrounding natural tissue upon implantation.

While the above-described elastic tubular substrate is a preferred structure for the manufacture of vascular prostheses, it should be clear that many other types of elongate substrates may be coated in accordance with the teachings disclosed herein. Thus, the non-compacted porous fabric tube of FIG. 1A may be used if desired, and other types of porous or non-porous tubes, planar webs, threads, fibers, and the like may also be coated. In general, the substrate should be composed of an organic material which can form carbon-carbon and carbon-fluorine covalent bonds. Thus, the process can coat stretched or non-stretched polytetrafluoroethylene, amides, esters, vinyls, rubbers and other types of polymeric substrates. Because a uniform, void-free, biocompatible surface coating may be applied in accordance with the process disclosed herein, the process permits the use of materials which heretofore have been considered unsuitable for the manufacture of implantable devices because of their tendency to produce thrombi or inflammation.

Coating Apparatus

Figure 3:
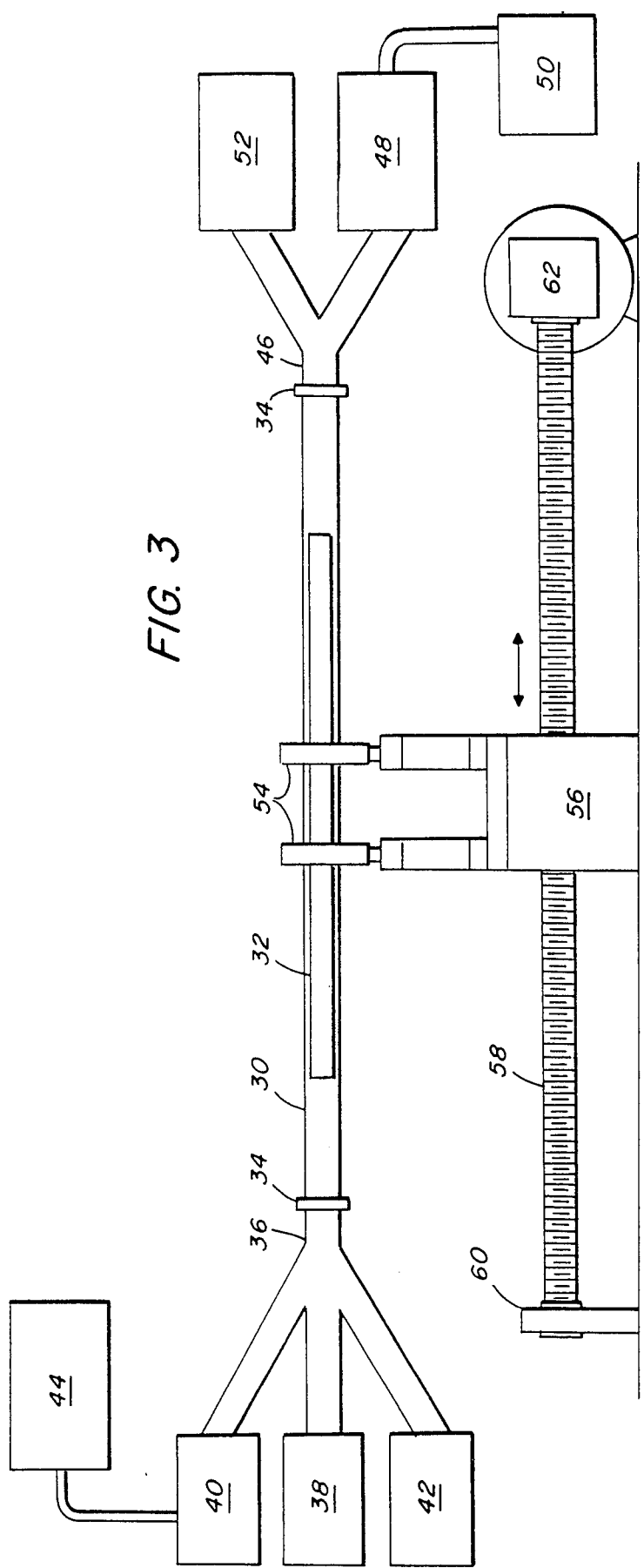
FIG. 3 diagrammatically illustrates apparatus used for practicing the plasma discharge coating method.
Figure 4:
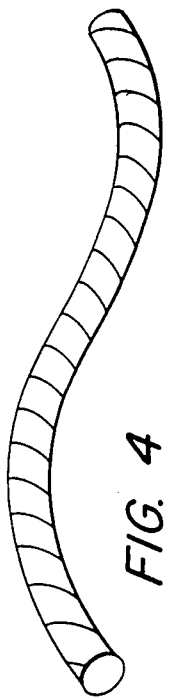
FIG. 4 depicts a coated fabric tube manufactured in accordance with the process disclosed herein.

FIG. 3 schematically illustrates apparatus useful in coating substrates intended for implantation. The reaction vessel comprises an electrically insulating, preferably glass tube 30. When coating tubular substrates to make vascular implants, the inside diameter of the tube 30 is selected to fit the outside diameter of the tubular substrate, here illustrated at 32. The annular space between the outside of substrate 32 and the inside of tubular reactor 30 should generally be no greater than one mm and preferably less than 0.2 mm if both the inside and the outside of a porous tube are to be coated. If the space between a tubular substrate and the reaction vessel is greater than about 1 mm, the uniformity and composition of the coatings applied generally are unsatisfactory, presumably because of the resulting alteration of gas flow patterns. Different diameter reactor tubes may be interchanged with the illustrated tube 30 for treating different diameter tubular substrates and non-tubular substrates by unfastening seals 34. When coating linear or planar elongate substrates, the tube diameter is less critical as there is little restriction to gas flow. Such non-tubular substrates are preferably disposed axially within the tube 30 held by any conventional clamping means (not shown).

Inlet end 36 of tubular reactor 30 is attached to a loading station 38 for loading the tubular substrate into the vessel, a mass flow controller 40 and an input-pressure sensor 42. Flow controller 40 is fed by a source 44 of a fluorinated gas, e.g., tetrafluoroethylene. The outlet end 46 of tubular reactor 30 is serviced by a vacuum controller 48 and a vacuum pump 50. Outlet pressure in the tube 30 is monitored by outlet-pressure sensor 52.

Glow discharge is induced within tubular reactor 30 by a pair of band electrodes 54 disposed about tube 30 and mounted on a traveling block 56. An RF coil could be substituted for the electrodes. Block 56 is threaded on an elongate screw 58 mounted for rotation in support 60 and driven by a variable speed, reversible electric motor 62. When the motor 62 is actuated, screw 58 transports traveling block 56 and its associated electrodes 54 at a constant velocity along the length of tubular reactor 30.

The tubular substrate 32 may be loaded into the reaction vessel 30 by opening loading station 38 and feeding the substrate tube with the aid of suction from vacuum controller 48. After sealing the loading station 38, the tube is evacuated and a flow of tetrafluoroethylene gas is established from flow controller 40 through the tube into vacuum controller 48. Pressure on the inlet end 36 and outlet end 46 of the reactor 30 is monitored by pressure monitors 42, 52, respectively. To establish gas flow there must necessarily be a pressure gradient along the length of the tubular reactor 30. After gas flow has been established, glow discharge is initiated in a portion of the volume of reactor 30 by actuating electrodes 54 to generate a radio frequency field within the tube 32, thereby inducing deposition of the fluorine-containing polymer coating on the substrate from the plasma generated by the RF field. The coating is progressively applied on the substrate surface by transporting the RF field progressively along the length of the tubular reactor 30 impelled by screw 58, preferably from right to left so that unreacted gas is available for reaction.

In order to achieve the uniform, high F/C ratio coating on substrates treated in the apparatus of FIG. 3, it is necessary to exercise control over the density of fluorine-containing gas molecules available for reaction adjacent the surface of the tube, to minimize or substantially eliminate the presence of oxygen and oxygen-containing compounds, and to control the RF field strength generated by electrodes 54 within rather narrow limits. This can be reproducibly accomplished because of the geometry of the tubular reactor 30 and its relationship to the substrate to be coated, and because the RF field which creates the plasma from the gas is moved relative to the substrate to progressively coat successive regions of the substrate. Using apparatus constructed in accordance with FIG. 3, as disclosed hereinafter, those skilled in the art will be able to routinely achieve the deposition of void-free fluorine-containing coatings along the lengths of the substrate surface which have a fluorine to carbon ratio in excess of 1.5. Typically, the F/C ratio of the coating along the length of the substrate will vary somewhat due to the pressure gradient along the tube. However, given a proper static inlet and outlet pressure, a porous tube having an outside diameter of 5 mm and a length of 1 meter can be coated on its interior with a covalently bonded, cross-linked fluorine-containing polymer having an F/C ratio greater than 1.5, which ratio differs no more than 10–12% along the length of the tube. For smaller diameter tubes, the variation in F/C ratio along the length of the tube may be greater.

This variation in F/C ratio may be minimized by regulating the amount of gas released into the tube as the RF field traverses the tube by adjusting flow controller 40, by increasing the vacuum drawn through vacuum control 48, or by some combination of the two. This technique permits one to compensate for the decreasing gas pressure and gas density in the downstream directions in the tube by altering gas flow progressively or periodically such that the density of available molecular species in the moving RF field remains more or less constant as the field traverses the reactor. Employing non-tubular substrates such as fibers, threads, or planar webs, the F/C ratio variation along the length of the substrate is smaller as there is far less restriction to flow, and uniformity of the coating is achieved more easily.

In accordance with the invention an excellent vascular graft can be produced which has an interior lumen whose surfaces are extraordinarily nonthrombogenic and has an exterior surface which minimizes inflammatory response upon implantation. The vascular graft has an inside surface coated with a fluorine-containing polymer having an F/C ratio in all regions above 1.5, its outside surface is coated with a fluorine-containing polymer having a lower ratio, e.g., 0.5. Preferably, the substrate used is a microporous fabric tube, knitted, woven, or nonwoven, made of known materials, preferably polyethylene terephthalate. The currently preferred substrate is the elastic tube describe in detail above.

To coat the tube, a suitable pressure differential is established at the inlet 36 and outlet 46 of tubular reactor 30 with tetrafluoroethylene gas flow set at a suitable rate as described below. With the substrate tube 32 in close fitting relation to the interior walls of tubular reactor 30, the fluorine-containg gas flows along the length of the lumen of the substrate, and a portion of it diffuses through the porous walls. The RF field generating device, in FIG. 3 depicted as a pair of spaced apart electrodes 54, is then moved along the length of the tube, preferably from its outlet end 46 to its inlet end 36, resulting in the creation of a plasma within a portion of the volume of the reactor 30, both inside and outside of the tubular substrate 32.

The density of available reactive species adjacent the interior walls of the tubular substrate is such that a coating having a high F/C ratio is uniformly deposited over the tube's interior surface. Within the pores traversing the wall of the substrate, a coating which exhibits an F/C ratio gradient decreasing from the interior wall toward the exterior wall is formed, and on the outside surfaces of the tube a coating with a significantly lower F/C ratio than that of the interior surfaces is produced. Thus, on surfaces of the tube designed for contact with blood, the coating is of very low energy, and substantially nonthrombogenic, whereas, at exterior surfaces, the coating is inert and noninflammatory, making it well suited for tissue ingrowth. Experiments with such tubes implanted in animals indicate that the tubes are characterized by outstanding patency and biocompatibility.

As noted above, the process may be used to deposit a high F/C ratio coating on other substrate shapes. Generally, because fibers and planar webs present fewer flow restrictions than tubes, the coating can be deposited as disclosed hereinafter relatively easily by empirically determining suitable plasma polymerization reaction parameters. Accordingly, in view of the disclosure which follows of how those parameters may be determined to result in the deposition of the high fluorine content coating on tubular substrates, which represent a most difficult case, those skilled in the art will be able readily to achieve the novel coating on other substrates.

Determining Glow Discharge Coating Parameters

The factors which control the F/C ratio of the coating are the type of gas used, the gas flow rate and pressure, and the RF field strength. These factors can be expressed by W/FM, where W denotes discharge power (which is proportional to field strength), F is the flow rate of the gas, and M is the molecular weight of the gas. The F/C ratio varies with any given gas as the values of W/FM vary. To obtain an F/C ratio higher than 1.5, W/FM generally must be within the range of $5 \times 10^7$ jouls/Kg to $2 \times 10^8$ joules/Kg. The coatings of the invention have been achieved using a pair of aluminum straps electrodes 2.5 cm apart, 2 mm from the central axis of the reactor tube, while applying 10–100 watts of power. In the examples disclosed herein, an external capacitive electrode couple was used, powered at 13.56 megahertz.

The RF field produced by such an apparatus obviously can be generated by different types of electrodes, and as noted above, a radio frequency coil may be used. Plasma or glow discharge can be produced by many available sources of radio frequency or microwave excitation or with electrode systems. The radio frequency commonly used is 10 kilohertz to 20 megahertz. Wattage or operating power can vary generally between 0 and 1000 watts.

To obtain the coating on the interior lumen of a tube, the inside diameter of the tube must be taken into account. For example, an 8 mm tubular substrate disposed in a tubular reaction vessel having an inside diameter of 8.2 mm, can be coated on its interior surface with a covalently bonded, cross-linked fluorine-containing polymer having an F/C ratio greater than 1.5 by applying 50 watts of power to the electrodes, moving the RF field at a rate of 40 cm per minute, and flowing pure tetrafluoroethylene gas at a rate of 7 cubic centimeters per minute (as measure at standard temperature and pressure, SCCM) through the tube. Inlet pressure should be maintained at 300 millitorr; outlet pressure at about 100 millitorr. These conditions will not produce high F/C ratio coatings on smaller diameter tubes. For example, for 4 mm tubes, the inside diameter of the reaction vessel should be about 4.2 mm, flow rate 4 SCCM, inlet pressure about 500 millitorr, and outlet pressure 100 millitorr.

Attempts to discern a relationship between tube diameter and length, field strength, flow rate, and speed of travel of the RF field which would enable prediction of successful coating parameters have been unsuccessful. However, for a substrate of a given shape these variables may be determined empirically. Once the parameters are set, coatings may be applied on as many individual substrates of the same type as desired.

The table set forth below defines a set of discharge powers, tetrafluoroethylene monomer flow rates, and inlet pressures (6.2 mm tubular reactor containing a 6 mm porous fabric tubular substrate) which result in an interior plasma deposited coating. In the table, DP refers to discharge power in watts, FR refers to actual flow rate, in standard cubic centimeters per minute, and P represents the pressure of the system at the inlet end detected by the pressure monitor in millitorr. A plus sign indicates that glow discharge was achieved; a minus sign indicates the absence of a glow discharge; a double plus sign indicates the region wherein a coating having a fluorine to carbon ratio greater than 1.5 on the inside surface of the tube is produced.

TABLE 1

| FR | 1 | 2.5 | 5.0 | 10 | 15 | 25 |
|---|---|---|---|---|---|---|
| P | 167 | 250 | 360 | 510 | 610 | 930 |
| DP |  |  |  |  |  |  |
| 10 | − | − | − | − | − | − |
| 25 | − | ++ | ++ | ++ | + | − |
| 50 | − | ++ | ++ | ++ | + | − |
| 75 | − | + | + | ++ | + | − |
| 100 | + | + | + | + | + | + |

To determine the parameters which will achieve the high F/C ratio coating for a given system, it is best to run a series of tests with the particular substrate involved starting with an energy input in the vicinity of $1 \times 10^8$ joules/Kg, a flow rate of 2–10 standard cubic centimeters per minute, and a pressure at the inlet end on the order of 200–500 millitorr. By independently varying discharge power, flow rate and/or pressure, a set of parameters become evident which produce the desired high fluorine content, low surface energy coating. For substrates in excess of about 15 cm long, it may be necessary to alter the flow rate of the gas as the RF field traverses the tubular reactor to minimize variations along the length of the substrate. The flow rate of the gas has been determined to be one of the most important variable in controlling the F/C ratio of the coating. Changes in the ratio are the most sensitive to this parameter. Coating thickness depends primarily on the time duration of the glow discharge per unit area of the substrate. In the preferred system wherein the field is transported, this correlates to the speed of movement of the RF field.

A fluorine to carbon ratio greater than 1.5 is most readily achieved if oxygen or oxygen-containing compounds are absent or present at only low concentration. Using tetrafluoroethylene gas, coatings having an F/C ratio as high as 1.98 have been produced. These outstanding results require the use of a gas having a fluorine to carbon atomic ratio of 2 or more. Tetrafluoroethylene, $C_2F_4$, is currently preferred. The coating may also be deposited from $C_3F_8$ with addition of hydrogen. The fluorine to carbon ratio in a given coating may readily be determined by conventional assay techniques, e.g., electron spectroscopy for chemical analysis (ESCA).

The preferred coatings of the invention have a water contact angle, as measured using a goniometer on water drops disposed on coated surfaces, greater than 120°. In fact, the higher ratio coatings have water contact angles of 140° to 150°. Generally, coatings applied in accordance with the process disclosed herein result in water contact angles equal to or greater than polytetrafluoroethylene surfaces. The water contact angle of the coating surface will depend on the particular F/C ratio of the applied coating, and on the geometry and microstructure of the substrate. Porous and non-porous substrate materials, or texturized and smooth substrate materials, having identical coatings will nevertheless have different water contact angles. Stretched polytetrafluoroethylene vascular grafts coated as disclosed herein typically exhibit little or no change in surface properties versus uncoated grafts. Polytetrafluoroethylene sheets having a water contact angle of about 108° exhibit an angle of 112°–130° when coated. The surfaces of polyvinyl chloride and polyethylene tubing can be coated to achieve significant increases in water contact angle. PVC catheters having inside surfaces characterized by an angle of 120° to 130° are possible.

The invention will be further understood from the following nonlimiting examples.

EXAMPLE 1—7.4 mm COATED GRAFT

A polyethylene terephthalate flat ribbon woven fabric tube of warp yarns (3 ply 50 denier/72 filaments) and fill yarns (single ply, 100 denier/96 filaments) in a simple weave pattern was loaded onto a teflon-coated stainless steel mandrel. The tube, having an inside diameter of about 6.5–7.0 mm, was loaded onto a 6.7 millimeter (outside diameter) mandrel. The contact between the mandrel and tube material was such that all fibers are pulled and stretched to create a smooth, consistent pattern, elimating any loose spots or wrinkling. The loaded mandrel was then heat set at 380° F. for 15 minutes to reduce further any looseness of the fabric and to create a smooth internal surface. After cooling, a monofilament of medical grade polypropylene was helically wrapped around the fabric for external support. The polypropylene wrapped fabric was then subjected to heat (380° F. for 5 minutes) to melt and subsequently attach the polypropylene to the fiber structure of the fabric. After cooling, the fabric was mechanically axially compressed so as to minimize the gap between individual circumferential threads or yarns creating a tightly compacted smooth internal surface in contact with the mandrel. The external threads not constrained from radial movement by the fixed wall of the mandrel were thereby deformed to produce radially outwardly spaced loops. These loops create an elasticity in the axial direction improving handling characteristics of the synthetic graft. This external surface also promotes good tissue anchoring while the internal surface maintains a smooth flattened blood contact surface. The compacted tube was then subjected to an elevated temperature (e.g., 360° F. for 3 minutes) to heat set this microscopic loop structure imparting a "memory" to the individual threads.

This compaction procedure converted a 110 cm tube which is inelastic to a 80 cm elastic tube.

After all processing steps, the compacted fabric tube was washed in pyrogen-free detergent water to remove any contaminants. After drying and dehumidification, the elastic fabric tube was ready for coating.

The fabric tube was then loaded into a glass tube that forms the reaction vessel of the plasma deposition system. The ratio of the inside diameter of the glass tube to outside diameter of the fabric tube was about 1.1 to 1. In this case, the outside diameter of the compacted fabric tube was about 8.1–8.3 mm, and the inside diameter of the glass tube was about 8.9 mm. A vacuum of $3 \times 10^{-3}$ mm Hg was then imposed on the plasma system by pumping out gas from one end of the tubular reactor to substantially eliminate any oxygen present. A monomer gas, in this case tetrafluoroethylene, was fed into the system by a mass flow controller from the other end of the tube. The gas flow rate was 7 standard cubic centimeters per minute. The pumping speed and rate was adjusted to produce a system pressure of 500 millitorr at the inlet end and about 300 millitorr at the outlet end. The pressure drop through the tube between the upstream and downstream ends creates a fluorine to carbon ratio gradient and an uneven thickness of polymer deposited onto the fabric tube due to varying energy and mass at each point. These variations over the length of the tube are no greater than about 10–12%. The F/C ratio of the coating ranged on the inside of the tube from 1.6–1.8. To control the F/C ratio further, the mass flow of monomer gas may be adjusted relative to the position of the energy input of the system so that the number of molecules polymerized is independent of the location or length of the plasma zone.

The energy input or discharge power is supplied by a pair of 6.3 mm wide aluminum band electrodes with an air gap of 2.5 cm which restricts the plasma zone. The electrodes were mounted on a traveling block which traverses the length of the tube to be coated at a speed of one cm per seven seconds. A power input of 50 watts was used. The coating is approximately 300 angstroms thick. A portion of the monomer gas passing through the tube traverses its pores. This results in a fluorinated coating on the outside surface of the tube which has a lower F/C ratio than the inside coating. After plasma polymerization, the elastic synthetic artery is removed from the reactor system, packaged, and sterilized.

EXAMPLE 2

A fabric tube of the type set forth in Example 1 about 60 cm long and having an outside diameter of about 10 millimeters was loaded into a 10 mm inside diameter glass tube and placed in the apparatus depicted in FIG. 3. An inlet pressure of 500 millitorr was established in the tube while maintaining a flow rate of tetrafluoroethylene gas of 10 sccm. Coating was conducted at a discharge power of 50 watts and an electrode velocity of one centimeter per 7 seconds. ESCA indicated that the fluorine to carbon ratio of the coating deposited on the inside of the tube was 1.7.

EXAMPLE 3

A silver coated crystal, 10 mm in diameter, was placed in a 12 mm ID reactor tube. The crystal was coated by flowing tetrafluoroethylene gas at 7 sccm at a pressure of 300 millitorr, and moving the electrode at 1 cm/7 seconds while maintaining a discharge power of 50 watts. ESCA of the surface of the crystal indicated the coating was rich in $CF_3$, $CF_2$, and CF species and had an F/C ratio of 1.6. No oxygen could be detected in the coating. Since no carbon or hydrogen was available on the silver surface, this example demonstrates that the process deposits an overcoating of fluorocarbon polymer on a preexisting surface. This is to be distinguished from processes which treat surface layers of the existing substrate lattice so as to substitute fluorine or fluorine-containing species for atoms within the surface.

EXAMPLE 4

A Mylar film (trademark for Dupont's polyethylene terephthalate), one cm by 15 cm, was placed in a 10 mm ID glass tube, and coated under the following conditions: 25 watts discharge power, 300 millitorr inlet pressure, 10 sccm flow rate, 1.0 cm/7 seconds electrode velocity. The coating produced on the surfaces of the film uniformly had an F/C ratio in excess of 1.5. The water contact angle on the uncoated film was about 60°, whereas after coating the angle increased to 108°. ESCA revealed a coating rich in $CF_3$, $CF_2$, and CF.

EXAMPLE 5

A piece of non-porous polyethylene tubing 50 cm long having an inside diameter of 3.3 mm was provided with a uniform, low energy surface coating extending along the length of its interior surface using the apparatus of FIG. 3 fitted with a glass tube having an inside diameter matching the outside diameter of the tubular substrate. A tetrafluoroethylene gas flow of 20 sccm at an inlet pressure of 300 millitorr was established, and the coating was applied using 30 watts of power while moving the electrode at a rate of 1 cm per 7 seconds. This resulted in deposition of a uniform, void-free fluorinated coating. The integrity of the coating was assessed by circulating an oil soluble dye (sudan red) through the coated tube and an uncoated polyethylene control tube for one hour. The tube samples were then both thoroughly washed to remove residual dye. The interior of the coated tube was uniformly impervious to the red dye whereas the uncoated tube was uniformly stained a deep red color.

The invention may be embodied in other specific forms without departing from the spirit and scope thereof. Accordingly, other embodiments are within the claims which follow:

What is claimed is:

1. A method of producing a tubular vascular prosthesis having a substantially non-thrombogenic inside surface and a biocompatible outside surface, said method comprising the steps of:
   A. placing an elongate organic tubular substrate defining pores and having a selected outside diameter within a tubular reaction vessel;
   B. establishing a flow of a fluorine-containing gas through said tubular substrate at a subatmospheric pressure;
   C. permitting a portion of said gas to diffuse through said pores in transit through said tube;
   D. applying an RF field to a portion of the volume of gas within said reaction vessel to produce glow discharge; and
   E. inducing relative motion of said RF field and said tubular substrate to deposit along the length of said substrate a substantially non-thrombogenic, polymerized, cross-linked coating bonded to the inside surface of said substrate having a first F/C atomic ratio and a biocompatible, polymerized, cross-linked coating bonded to the outside surface of said substrate having an F/C atomic ratio lower than said first ratio wherein deposition of said polymerizable coating is controlled by controlling the pressure and flow rates of said gas and the field strength of said RF field.

2. The method of claim 1 wherein the flow established in step B is controlled to maintain a substantially constant density of available reactive species of said fluorine-containing polymerizable gas at inside surfaces of said substrate and within said RF field during relative motion to produce a cross-linked coating having a substantially uniform F/C ratio along the length of the inside surface of said substrate.

3. The method of claim 1 wherein the tubular reaction vessel has an inside diameter less than one mm than the outside diameter of said tubular substrate.

4. The method of claim 1 wherein said fluorine containing gas is substantially free of oxygen and oxygen containing compounds.

5. The method of claim 1 wherein the RF field is moved along the length of said substrate.

6. The method of claim 1 wherein the gas comprises a gas having a fluorine to carbon atomic ratio of at least 2.0.

7. The method of claim 6 wherein said gas comprises tetrafluoroethylene.

8. The method of claim 1 wherein the deposition of polymerized coating is controlled to produce a coating having an F/C ratio greater than 1.5 bonded to the inside surface of said substrate.

9. The method of claim 1 wherein said substrate comprises a fabric tube.

10. The method of claim 9 wherein said fabric tube comprising threads composed of fibers less than approximately 15 microns in diameter.

11. The method of claim 9 wherein said fabric tube has a wall thickness less than about 0.60 mm.

12. The method of claim 9 wherein said fabric is a knitted fabric.

13. The method of claim 9 wherein said fabric is a woven fabric.

14. The method of claim 9 wherein said fabric is a non-woven fabric.

15. The method of claim 1 wherein said substrate comprises polyethylene terephthalate.

16. The method of claim 9 wherein said fabric tube comprises circumferentially oriented fill threads and longitudinally oriented warp threads defining loops extending radially from between said fill threads, said loops being set to return to a loop configuration upon the release of axial stress on said tube.

17. The method of claim 1 wherein said tubular substrate is elastic.

18. A method of coating an elongate organic substrate to produce a uniform non-thrombogenic surface thereon having an F/C ratio greater than 1.5, said method comprising the steps of:
   A. placing said elongate organic substrate within a tubular reaction vessel;
   B. establishing a flow of a fluorine containing gas having an F/C atomic ratio of at least two through said vessel and about said substrate at a subatmospheric pressure;
   C. applying an RF field to a portion of the volume of gas within said vessel to produce glow discharge;
   D. inducing relative motion of said RF field and said elongate substrate while controlling the density of available reactive species from said gas in the volume of said glow discharge adjacent a surface of said substrate to deposit along the length of said substrate a substantially uniform, non-thrombogenic, polymerized, cross-linked, fluorine-containing coating having an F/C ratio greater than 1.5.

19. The method of claim 18 wherein the RF field is moved along the length of said substrate.

20. The method of claim 18 wherein said fluorine-containing gas is tetrafluoroethylene.

21. The method of claim 18 wherein said gas is substantially free of oxygen or oxygen containing compounds.

22. The method of claim 18 wherein said elongate substrate comprises polyethylene terephthalate.

23. The method of claim 18 wherein said substrate comprises a fabric.

24. The method of claim 19 wherein the density of available reactive species is controlled to be substantially constant at the surface of said substrate in the area of glow discharge by varying gas pressure at a gas inlet end of said tubular vessel.

25. The method of claim 19 wherein the density of available reactive species is controlled to be substantially constant at the surface of said substrate in the area of glow discharge by varying gas pressure at a gas inlet end and a gas outlet end of said tubular vessel.

* * * * *